United States Patent
Rakshit (10) Patent No.: US 11,647,982 B2
(45) Date of Patent: May 16, 2023

(54) INSTRUMENT UTILIZATION MANAGEMENT

(71) Applicant: International Business Machines Corporation, Armonk, NY (US)

(72) Inventor: Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 910 days.

(21) Appl. No.: 16/574,968

(22) Filed: Sep. 18, 2019

(65) Prior Publication Data
US 2021/0077070 A1    Mar. 18, 2021

(51) Int. Cl.
*A61B 8/00* (2006.01)
(52) U.S. Cl.
CPC .............. *A61B 8/4254* (2013.01); *A61B 8/46* (2013.01)
(58) Field of Classification Search
None
See application file for complete search history.

(56) References Cited

U.S. PATENT DOCUMENTS

| 9,351,782 | B2 * | 5/2016 | Stein | A61B 34/30 |
| 10,636,323 | B2 * | 4/2020 | Buras | G16H 30/20 |
| 2014/0135616 | A1 * | 5/2014 | Stein | A61B 17/92 |
| | | | | 600/424 |
| 2014/0276069 | A1 | 9/2014 | Amble | |
| 2015/0051489 | A1 | 2/2015 | Caluser | |
| 2015/0366628 | A1 * | 12/2015 | Ingmanson | A61B 90/37 |
| | | | | 600/424 |
| 2016/0113632 | A1 * | 4/2016 | Ribes | A61B 8/5269 |
| | | | | 600/440 |
| 2018/0225993 | A1 * | 8/2018 | Buras | A61B 34/20 |
| 2019/0076120 | A1 | 3/2019 | Shoudy | |
| 2019/0117999 | A1 | 4/2019 | Fontanarosa | |

OTHER PUBLICATIONS

"Automated Ultrasonic Testing (AUT)," Corrosionpedia, Corrosion & Prevention Conference and Exhibition, Nov. 24, 2019, 2 pages. <https://www.corrosionpedia.com/definition/4456/automated-ultrasonic-testing-aut>.
"Automated Ultrasonic Testing (AUT)," Stanley Inspection, printed Sep. 9, 2019, 1 page. <http://www.stanleyinspection.com/services/automated-ultrasonic-testing-aut>.
"Invenia ABUS," GE Healthcare, printed Sep. 9, 2019, 6 pages. <https://www.gehealthcare.com/products/ultrasound/somo-v-abus-breast-imaging/invenia-abus>.
"Ultrasound, ultra-simplified. Discover Butterfly iQ" Butterfly Network, printed Sep. 9, 2019, 9 pages. <https://www.butterflynetwork.com/?gclid=EAIaIQobChMIkMjc953D4QIVK7bACh3tUASREAAYASAAEgLGxfD_BwE>.

* cited by examiner

*Primary Examiner* — Luther Behringer
(74) *Attorney, Agent, or Firm* — Brian D. Welle (57) ABSTRACT

Aspects of this disclosure relate to directing the movement of instrument such as medical devices. For example, data regarding an ongoing physical of an instrument that is configured to gather spatial data via physical manipulation of the instrument for a procedure is received. A current orientation of the instrument is determined. Additional spatial data to gather for the procedure is determined. A subsequent physical manipulation on how to physically maneuver the instrument relative to the current orientation to gather the additional spatial data is determined. Real-time feedback on how to execute the subsequent physical manipulation is provided.

10 Claims, 4 Drawing Sheets

INSTRUMENT UTILIZATION MANAGEMENT

BACKGROUND

Different types of medical images may be captured by manually moving an instrument. For example, an ultrasound probe for capturing ultrasound images of a patient may be physically manipulated around and accordingly an ultrasound image will be captured. A quality and coverage of captured spatial data of the target area may depend on how the ultrasound probe is physically manipulated around the affected area. If the ultrasound probe was poorly physically manipulated during the procedure, then the spatial data may not be captured properly and accordingly an ability to detect conditions of the spatial data may be reduced.

SUMMARY

Aspects of the present disclosure relate to a method, system, and computer program product relating to managing the movement of an instrument. For example, the method may include receiving data regarding an ongoing physical manipulation of an instrument that is configured to gather spatial data via physical manipulation of the instrument for a procedure. The method may further include determining a current orientation of the instrument is determined. Additional spatial data to gather for the procedure. The method may further include determining a subsequent physical manipulation on how to physically maneuver the instrument relative to the current orientation to gather the additional spatial data. The method may further include providing real-time feedback on how to execute the subsequent physical manipulation. A system and computer product configured to perform the above method are also disclosed.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to managing the physical manipulation of an instrument, while more particular aspects of the present disclosure relate to providing real-time feedback regarding how to physically manipulate an instrument during operation to capture a predetermined set of spatial data. While the present disclosure is not necessarily limited to such applications, various aspects of the disclosure may be appreciated through a discussion of various examples using this context.

Advancements in technology have resulted in a large number of complex instruments that may be used to gather precise sets of spatial data in executing complex procedures. For example, a person may use an instrument that gathers diagnostic information via the physical manipulation of that instrument through a three-dimensional (3D) space. Examples of such complex instruments may include precise laser-scanning instruments, ultrasound instruments, x-ray instruments, or the like. These instruments may gather spatial data that indicates density data, shape data, location data, or the like of one or more objects in a 3D target area. Given the increasingly connected state of the world, it may be increasingly possible for a layperson that is not fully trained on these complex instruments to get access to smart diagnostic instruments, and attempt to execute the complex procedures themselves. The layperson may then send the gathered spatial data to a specialist for analysis/diagnosis.

Instruments may be used for predetermined procedures, during which the instruments analyze predetermined objects for predetermined conditions. The gathered spatial data may relate to these predetermined conditions. For example, where the instrument is an ultrasound probe and the procedure is a neonatal ultrasound, a medical professional may analyze a plurality of factors of the spatial data gathered by the ultrasound to identify a plurality of medical conditions of a fetus, such as a biological gender, a presence or absence of some heart defects or kidney problems, or the like.

In some examples, an accuracy and/or fidelity of the gathered spatial data may be affected by the manner in which the instrument was physical manipulated during the procedure in which the instrument gathered the spatial data. For example, an ultrasound image as captured by an ultrasound probe may be more or less accurate depending on whether the ultrasound probe was in a certain location along a certain trajectory at a certain speed and/or stayed at a certain location for a certain amount of time during the procedure in which the probe gathered the ultrasound image. It may be difficult or impossible for an untrained user (e.g., a non-medical professional with access to an ultrasound probe) to physically manipulate the instrument in the proper direction along the various vectors while maintaining the appropriate speed and/or pauses that may improve the accuracy and/or fidelity of the gathered spatial data.

Aspects of this disclosure relate to providing a user real-time feedback as a user physically manipulates an instrument to improve an accuracy and fidelity of spatial data gathered by the instrument. A computing controller (hereinafter referred to as a controller) that includes a processor configured to execute instructions stored on a memory may provide this feedback. The controller may be integrated into the instrument or the controller may be a part of a separate computing device that is communicatively coupled to the instrument. The controller may provide this feedback using the spatial data gathered by the instrument, and/or the controller may provide this feedback using sensors (e.g., accelerometers, pressure sensors, or the like) in the instrument.

The controller may provide real-time feedback for a plurality of potential physical manipulations. For example, the controller may provide a queue that the user is to physically manipulate the instrument by holding the instrument at a location, moving the instrument in a direction, moving the instrument along a vector or trajectory, moving the instrument at a speed, or the like. The controller may provide this feedback with a plurality of guidance elements of the instrument. For example, the controller may utilize guidance elements that include pico-projectors that project visual feedback (e.g., such as arrows or the like) that provide visual indications as projected onto the instrument and/or onto the environment (e.g., such as on a body of a patient). Additionally, or alternatively, the guidance elements may provide haptic feedback or auditory commands or the like to provide queues to the user. In some examples, the controller may utilize a screen of a user device to provide queues to the user. For example, the user device may depict some of the spatial data gathered by the controller, and the controller may cause some queues to overlay the depiction of the spatial data to provide context to how (and why) the user is to physically manipulate the instrument (e.g., such that the user knows to physically manipulate the ultrasound probe in a different direction to try to ascertain whether or not a fetus depicted by the spatial data has a cleft lip). Additionally, or alternatively, the controller may utilize one or more augmented reality (AR) devices to overlay one or more queues over the environment. In this way, aspects of the disclosure may be configured to improve an ability of a system to provide feedback and/or queues on how the instrument should be physically manipulated to increase a chance of gathering accurate spatial data.

Figure 1:
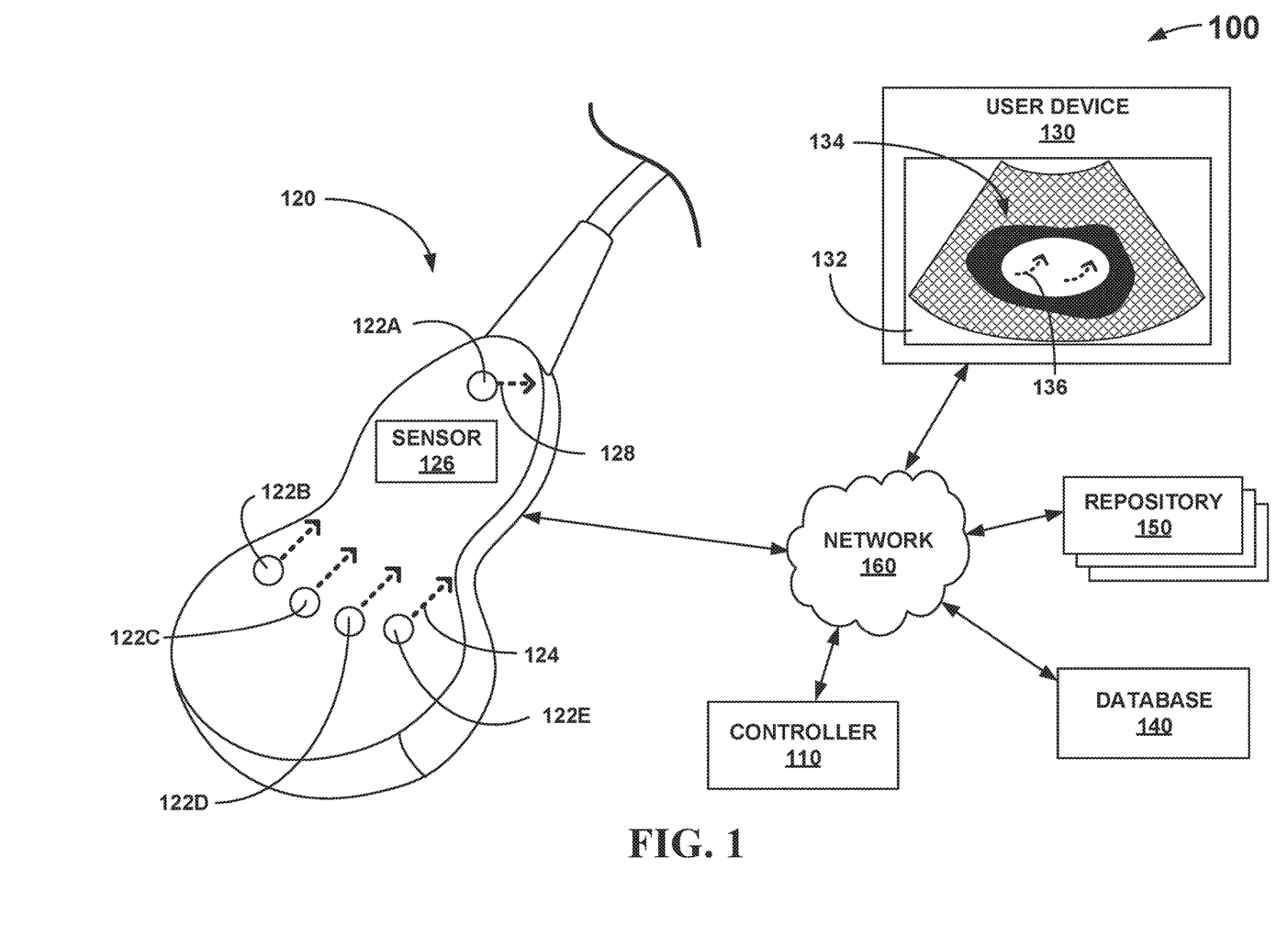
FIG. 1 depicts a conceptual diagram of an example system in which a controller may provide feedback regarding the physical manipulation of an instrument.

For example, FIG. 1 depicts system 100 that includes controller 110 similar to the controller described above. Controller 110 may include a computing device, such as computing device 200 of FIG. 3 that includes a processor communicatively coupled to a memory that includes instructions that, when executed by the processor, cause controller 110 to execute the operations described below. Controller 110 may be configured to manage physical manipulation of instrument 120 for a procedure. Instrument 120 may include a physical tool that is configured to be moved in a 3D space to gather 3D data, such as an ultrasound probe, a precision laser scanner, an X-ray device, or the like.

In some examples, as depicted in FIG. 1, controller 110 may be within a separate discrete housing in relation to instrument 120. For example, controller 110 may be integrated into a laptop or desktop or server or rack of servers or the like that is configured to communicate with (e.g., receive data from and send commands to) instrument 120. In other examples (not depicted), controller 110 may be integrated into a housing of instrument 120. For example, instrument 120 may be an ultrasound probe or the like, and a processor and memory of controller 110 may be stored within instrument 120. In other examples, some portions of controller 110 as described herein may be stored (whether permanently or temporarily) within instrument 120 while other portions are stored within a physically separate computing device. For example, some portions of controller 110 may be stored within a dongle or the like that is inserted into instrument 120 to communicate with and/or control instrument 120, while another portion of controller 110 is stored on a separate computing device.

As described herein, instrument 120 may be a diagnostic tool configured to gather data as part of a procedure. The data may include spatial data, such as density data or hardness data through a 3D space, or volumetric shape data through a 3D space, or the like. Instrument 120 may be configured to gather spatial data for one or more predetermined procedures, where the procedure further relates to a predetermined target area across which spatial data is to be gathered. Further, each procedure may include detecting for one or more conditions of the target area. For example, instrument 120 may include an ultrasound probe, and the procedure may include a neonatal ultrasound, and the conditions may include one or more medical conditions that the fetus may have and/or a biological gender of the fetus or the like. For another example, instrument 120 may include an X-ray device, and the procedure may include an X-ray of an area to determine if any broken bone conditions are detected. For another example, instrument 120 may include a high-precision laser scanning device, and the procedure may include scanning a surface of a manufactured item to verify if tolerance conditions were maintained. Other examples consistent with this disclosure are also possible.

Controller 110 may detect that instrument 120 currently is or is about to be physically manipulated to gather data for a procedure. Controller 110 may detect this via instrument 120 turning on (e.g., via a power switch, or via a power cord of instrument 120 being plugged into an outlet, or the like), instrument 120 and/or a user sending a request (e.g., a request to begin managing physical manipulation) to controller 110, or the like. Controller 110 may determine a procedure that instrument 120 is executing. Controller 110 may determine the procedure through the procedure being identified in the request as sent to controller 110. Alternatively, in some examples controller 110 may identify the procedure via the initial spatial data gathered by instrument 120 (e.g., as such data may indicate whether an ultrasound probe is conducting a neonatal ultrasound or a gallbladder ultrasound or the like). Alternatively, in some examples controller 110 may only be configured to manage physical manipulation of instrument 120 for a single procedure (such that in each instance controller 110 manages physical manipulation for that procedure).

Controller 110 may compare spatial data gathered by instrument 120 against template data stored in database 140 available to controller 110. Database 140 may include a computing device (similar to computing device 200 of FIG. 3) such as a server or a rack of servers or the like. Database 140 may include data that is relevant to controller 110, such as a type and amount of spatial data to effectively conduct one or more procedures, and/or various conditions to check for among each procedure. In some examples each procedure and related condition as stored in database 140 may include a predetermined amount of spatial data to gather. Further, in some examples, database 140 may store a manner in which spatial data is to be gathered for some or all procedures and/or conditions.

Controller 110 may analyze spatial data as being gathered by instrument 120 to verify that gathered spatial data satisfies data requirements of the procedure. Put differently, controller 110 may be configured to verify that gathered spatial data is sufficient to execute the procedure, including verifying a status of one or more conditions of the procedure. Controller 110 may validate this spatial data as captured by instrument 120 on a real-time basis, such that the spatial data is analyzed substantially immediately upon being gathered by instrument 120.

Controller 110 may validate the spatial data by confirming whether or not the spatial data satisfies one or more thresholds. For example, controller 110 may confirm whether or not the most recently gathered spatial data satisfies a threshold of what is good data, such that controller 110 may determine whether or not the spatial data that was gathered is adequate for the procedure. Where controller 110 determines that the gathered data fails the threshold, controller 110 may provide feedback as described herein for the user to gather better data. For another example, controller 110 may confirm whether or not the trajectory of the gathered spatial data satisfies a threshold of subsequent spatial data that will subsequently need to be gathered to complete the procedure. Put differently, controller 110 may determine whether or not instrument 120 is currently being physically manipulated along a trajectory or vector that will continue gathering needed spatial data, should instrument 120 continue this trajectory. Where controller 110 determines that instrument 120 is moving along a trajectory that will subsequently cause instrument 120 to gather noisy or unnecessary or otherwise suboptimal spatial data, controller 110 may provide feedback as described herein to direct user to change this trajectory.

Controller 110 may determine whether or not the previously gathered data is accurate by determining whether this spatial data satisfies a threshold. Specifically, controller 110 may determine that gathered spatial data satisfies a threshold by comparing the spatial data against a set of predetermined spatial data stored in database 140. The predetermined spatial data may include one or more shapes of data of one or more target objects, and may further identify a required accuracy threshold (as described below). For example, to continue the neonatal ultrasound example, the shape may be a shape of a fetus, such that controller 110 may determine that the gathered shape satisfies a threshold when the gathered spatial data includes a shape of a fetus as matched to various fetus shapes stored in database 140. The predetermined shape data may include a range of expected potential shapes, such that many or substantially all shapes that the target object (e.g., the fetus) may define, whether typical or atypical, may be detected as accurately reflecting the target object.

In some instances, controller 110 may determine whether or not the spatial data satisfies an accuracy or consistency threshold. For example, controller 110 may gather data points for each or many 3D points multiple times, such as taking a density measurement for each 3D point in space multiple times. Controller 110 may identify the spatial data for such a point as satisfying an accuracy threshold when the data for this point is within a consistency threshold, such as within 10% across time. For example, if a user moves instrument 120 too abruptly or does not hold instrument 120 flush against a patient or square towards a target object, each gathered spatial data may be relatively inaccurate, such that they change by 25% relative to each other. Controller 110 may identify such fluctuation as failing an accuracy threshold, and therein provide feedback to a user to re-gather such spatial data until the gathered spatial data satisfies the threshold.

Further, as mentioned above, controller 110 may be configured to identify whether a trajectory of instrument 120 satisfies a threshold. For example, in addition (or alternatively) to verifying whether gathered spatial data satisfies one or more thresholds as described above, controller 110 may verify whether or not a trajectory of instrument 120 indicates that subsequent spatial data that will be gathered by instrument 120 along this trajectory will satisfy a threshold. Controller 110 may determine that subsequent gathered spatial data along a trajectory will satisfy a threshold if the subsequent data relates to spatial data that relates to the procedure.

For example, to continue the neonatal ultrasound example, controller 110 may determine that subsequent spatial data along the trajectory satisfies the threshold if the spatial data is still related to the fetus, whereas if the data is not related to the fetus (e.g., it is of the womb or of an adjacent organ or the like) the data may fail a threshold. Alternatively, or additionally, controller 110 may determine whether or not the trajectory indicates that the subsequent spatial data is gathered at an angle and/or speed or the like at which the spatial data is reliable. If not, controller 110 may provide feedback as described herein to correct or otherwise improve a trajectory to thus improve the type or quality of subsequently gathered spatial data. For example, controller 110 may determine that subsequent spatial data will still be of the fetus, but that it may be gathered too quickly (e.g., as a result of instrument 120 moving along its trajectory fast) and/or that the instrument may not gather the data as cleanly as it might (e.g., as a result of instrument 120 needed to be rotated 90° as it moves along this trajectory). Controller 110 may provide queues as described herein to provide feedback to, e.g., slow down instrument 120, and/or rotate instrument 120, as it moves along this trajectory.

In some examples, controller 110 may provide queues that (if followed) are configured to cause instrument 120 to gather spatial data where a subsequent portion of a target object is predicted to be (e.g., where controller 110 has already identified a first portion of the target object). For example, controller 110 may be managing physical manipulation of instrument 120 of a procedure that relates to an object that follows an atypical shape, such as a target area of the intestines. Controller 110 may utilize sample target areas from database 140 (and/or repositories 150) as described herein to predict where a subsequent section of the target area will be, and predict instrument 120 to move to gather spatial data for where this predicted section. Further, controller 110 may predict and provide queues that are configured to cause instrument 120 to gather spatial data where an internal body part is configured to move to. For example, controller 110 may be managing physical manipulation of instrument 120 of a procedure of a fetus that is moving, and controller 110 may predict how the fetus may move and provide queues that are configured to direct instrument 120 to capture such movement. Other examples are also possible.

In some examples, controller 110 may store spatial data thresholds as relating to a sequential order of steps of a procedure. In such examples, controller 110 may first direct (and therein provide feedback toward) instrument 120 gathering data for a first step of the procedure, and then (after verifying the gathered spatial data as satisfying relevant thresholds) subsequently direct and verify spatial data from instrument 120 for a second step of the procedure, and so on. By dividing a procedure into steps, controller 110 may be configured to provide relatively clearer and more ordered feedback on physically manipulating instrument 120.

In certain examples, steps of a procedure may depend upon the gathered spatial data of the previous steps. For example, one step may include detecting whether or not the target object has one or more conditions (e.g., a cleft lip in the neonatal ultrasound example). If the gathered spatial data of that step indicates that one or more conditions is present, a subsequent step may include verifying that condition and/or determining a severity of that condition. Alternatively, if the gathered spatial data of that step indicates that no conditions are present, the subsequent step may include checking for a separate set of conditions. In this way, controller 110 may autonomously execute an algorithm to provide feedback for instrument 120 to efficiently gather all data required for a procedure.

Controller 110 may provide feedback for physical manipulation using one or more guidance elements 122A-122E (collectively, "guidance elements 122") on instrument 120. Guidance elements 122 may be configured to provide an indication to a user. For example, guidance elements 122 may include one or more pico-projectors that are configured to project an image that provides feedback. Alternatively, or additionally, guidance elements 122 may include haptic devices that are configured to vibrate or the like to provide feedback, audio devices that are configured to provide auditory feedback, or the like. Though pico-projector guidance elements 122 are predominantly described herein, it is to be understood that any guidance element 122 consistent with this disclosure may be used in other examples.

For example, controller 110 may determine that gathered spatial data failed one or more thresholds, such that instrument 120 should gather additional replacement spatial data. Controller 110 may identify a current orientation of instrument 120 which includes a relative trajectory of instrument 120. Controller 110 may analyze the previously gathered spatial data to identify the trajectory of instrument 120 (e.g., where the spatial data indicates a relative position of instrument 120). Additionally, or alternatively, controller 110 may identify a relative position and/or trajectory of instrument 120 using one or more sensors 126 of instrument 120. For example, sensor 126 may include an accelerometer or speedometer or the like that can be used to determine a movement vector of instrument 120, and/or sensor 126 may include pressure sensors that can determine how hard instrument 120 is pressing against a patient or the like. Controller 110 may cross-reference spatial data and data from sensor 126 to determine a current orientation and/or trajectory of instrument 120.

Once controller 110 determines the trajectory of instrument 120, controller 110 may determine a subsequent physical manipulation necessary to send instrument 120 in the preferred direction. Controller 110 may provide this feedback using guidance elements 122, as described herein. For example, controller 110 may cause pico-projector guidance elements 122 to depict queues such as directional arrows 124 or the like in the direction of the determined subsequent physical manipulation. These directional arrows 124 may be longer or shorter depending upon a desired speed at which controller 110 determines that instrument 120 should be moved (e.g., where a longer arrow depicts more speed, and a shorter arrow depicts less speed). Further, though directional arrows 124 are depicted as straight, in other examples, controller 110 may cause guidance elements 122 to provide angular arrows to indicate angular movements, or no arrows to depict to hold still, or the like.

In some examples, some guidance elements 122 may be secured to instrument 120 around a primary face of instrument 120 while one or more other guidance elements 122 may be secured along a longitudinal axis of instrument 120. For example, guidance element 122A is depicted as isolated along a handle of instrument 120, while guidance elements 122B-122E are along a primary face of instrument 120. In some examples, controller 110 may provide different types of feedback from different guidance elements 122. For example, guidance element 122A that is along a longitudinal axis of instrument may be configured to show angular direction 128 along which instrument 120 is to be twisted as instrument 120 moves in trajectory of directional arrows 124. In this way, a plurality of guidance elements 122 may provide feedback in multiple ways to increase an ability of controller 110 to cause instrument 120 to gather desired spatial data.

In some examples, guidance elements 122 may include pico-projectors that are configured to depict different colors as different types of queues to the user. Controller 110 may cause pico-projector guidance elements 122 to depict these different colors to provide different feedback. For example, different colors may indicate a speed at which instrument 120 is to be moved. Alternatively, controller 110 may cause guidance elements 122 to depict different text with different colors, such as a blinking red "STOP" text when controller 110 detects that instrument 120 should gather more spatial data at its current location. Alternatively, controller 110 may be configured to provide queues from guidance elements 122 in one color (e.g., green) when instrument 120 is being physically manipulated as directed, and provides queues in a different color (e.g., red) when instrument 120 is being physically manipulated in a manner that does match the feedback or queues from controller 110.

In some examples, sensor 126 may detect non-spatial data of the target area, which may be used to identify conditions of the procedure. For example, sensor 126 may include a temperature sensor or the like that can determine a condition of a patient during a neonatal ultrasound. Using such a temperature reading, controller 110 may determine various medical conditions of the patient to determine subsequent physical manipulations to execute one or more medical procedures. Additionally, or alternatively, sensor 126 may include a microphone or the like that may detect auditory responses from a patient, such as noises that may indicate discomfort or the like. Where sensor 126 is thusly configured to detect discomfort or the like, controller 110 may detect such discomfort and use this discomfort to analyze conditions (e.g., as discomfort may indicate one or more medical conditions).

In some examples, some or all gathered spatial data may be provided on user device 130. User device 130 may be a computing device (e.g., similar to computing device 200 of FIG. 3) such as a laptop or smart television or cell phone or the like. User device 130 may include a display 132 upon which the gathered spatial data is provided. For example, controller 110 may depict spatial data of target object 134 of the procedure. Though target area 134 as depicted as a simple oval in FIG. 1 for purposes of illustration, it is to be understood that target area may be any shape (as indicating any object) that is consistent with this disclosure. Spatial data as gathered may be immediately presented on display 132 of user device 130, such that a user may follow a real-time gathering of spatial data.

Controller 110 may be configured to provide feedback on display 132 of user device 130. For example, as depicted in FIG. 1, controller 110 may provide a queue such as directional arrows 136 on display 132. Directional arrows 136 generated on display 132 may correspond to directional arrows 124 generated by guidance elements 122, to provide comprehensive feedback. By providing numerous types of feedback on both a depicted image of the gathered spatial data on user device 130 and on instrument 120, controller 110 may improve an ability to indicate how to physically manipulate instrument 120 to gather relevant spatial data.

Controller 110 may be configured to substantially immediately identify conditions of the gathered spatial data and respond accordingly. For example, controller 110 may compare the gathered spatial data against the predetermined data sets of database 140, as described above. Further, where controller 110 identifies data that does not match data of database 140 but satisfies a threshold accuracy/consistency threshold (e.g., indicating that the gathered spatial data was not inaccurate, but rather reflects a real condition of target object 134), controller 110 may compare the gathered spatial data against one or more repositories 150 to determine a subsequent physical manipulation.

Repositories 150 may include one or more online medical databases or the like that may include the gathered spatial data. Controller 110 may utilize natural language processing (NLP) techniques and/or image recognition techniques as described herein to identify what the gathered spatial data indicates. Once identified, controller 110 may identify (whether from repositories 150 or database 140 or both) a subsequent physical manipulation to further execute a procedure as related to this additional condition. In some examples, once controller 110 identifies spatial data that does not match data of database 140 controller 110 may provide feedback using guidance elements 122 to hold in a static position, reacting appropriately once the nonmatching spatial data has been analyzed.

For example, controller 110 may identify (e.g., from repositories 150) that the nonmatching spatial data is a meaningless data artifact, therein dismissing the artifact and continuing with the procedure. Alternatively, controller 110 may identify the nonmatching spatial data and provide physical manipulations relating to it (e.g., as a result of controller 110 successfully identifying the nonmatching spatial data from repository 150 as a possible condition and further identifying follow-up steps from repository 150 on subsequent spatial data to gather on this possible condition). Alternatively, controller 110 may determine to flag the nonmatching spatial data for further analysis by a trained analyst (e.g., a medical analyst), subsequently moving to a next step in the procedure. However controller 110 responds to spatial data that controller 110 is unable to match, controller 110 may subsequently monitor how this unmatched spatial data is utilized by a trained analyst (e.g., a medical analyst), therein improving at responding to similar spatial data in the future. In this way, controller 110 may be configured to autonomously and immediately provide physical manipulation feedback in response to receiving most or substantially all spatial data, and further improve at doing so over time.

In such ways, controller 110 may improve at an ability to provide physical manipulation feedback over time. For example, controller 110 may use one or more machine learning techniques to identify relationships between spatial data, one or more patient symptoms (e.g., gathered using sensors 126 or the like), and relative conditions. As described above, controller 110 may reference repositories 150 or the like that include different types of spatial data of different types of procedures or symptoms. For example, to go back to the neonatal ultrasound example, controller 110 may regularly (e.g., every week or every day) consult online medical repositories 150 to identify records (e.g., using NLP) of patient's symptoms, different biometric conditions (e.g., feeling discomfort or pain), different response of the patients, or the like, therein comparing these against extracted recognize artifacts of the gathered spatial data. This may include such correlations as determining relative positions and/or dimensions of objects of ultrasound images.

Over time, controller 110 may create and update a knowledge corpus with these correlations. For example, controller 110 may correlate relative positions of different types of detected objects, different types of conditions of different types of objects, different dimensions of the objects, different movement patterns of the objects (e.g., where target object 134 is a mobile thing such as a fetus that is moving), different associated coverage areas, or the like. Controller 110 may then update procedures and conditions as stored in database 140. Updating these procedure and conditions may include updating a manner in which controller 110 analyzes the real-time quality and coverage of the gathered spatial data and therein provides feedback regarding the movement path of instrument 120 by, e.g., causing guidance elements 122 to show another direction (e.g., auto-correcting the movement of instrument 120). Using such techniques, controller 110 may improve over time at providing physical manipulation feedback.

Controller 110 may communicate over network 160. Network 160 may include a computing network over which computing messages and/or computing data may be sent and/or received. For example, network 160 may include the Internet, a local area network (LAN), a wide area network (WAN), a wireless network such as a wireless LAN (WLAN), or the like. Network 160 may comprise copper transmission cables, optical transmission fibers, wireless transmission, routers, firewalls, switches, gateway computers and/or edge servers. A network adapter card or network interface in each computing/processing device (e.g., controller 110, instrument 120, user device 130, database 140, and/or repositories 150) may receive messages and/or instructions from and/or through network 160 and forward the messages and/or instructions for storage or execution or the like to a respective memory or processor of the respective computing/processing device.

In some examples, guidance elements 122 may include pico-projectors that are joined in a flexible pivotal joint, so that the direction indicated by respective pico-projector guidance elements 122 can be changed as controlled by controller 110. For example, FIGS. 2A-2D depict side views 170A, 170C and top views 170B, 170D of pico-projector guidance element 190 (that is substantially similar to guidance element 122 with the exception of any differences described herein) on instrument 192 (that is substantially similar to instrument 120 with the exception of any differences described herein) as guidance element 190 pivots to provide directional arrows 124B, 124C (both of which are substantially similar to directional arrow 124 as described above) in different directions. Though pico-projector guidance element 190 is depicted as relatively large in comparison to instrument 192 for purposes of illustration, pico-projector guidance element 190 may be substantially any relative size compared to instrument 192 that is consistent with this disclosure.

Figure 2A:
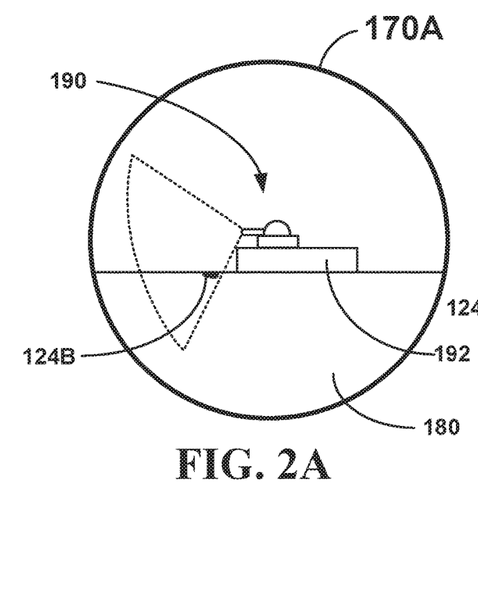
FIG. 2A depicts a side view of an example guidance element of an instrument that is actuated to provide a first indication in a first direction.
Figure 2B:
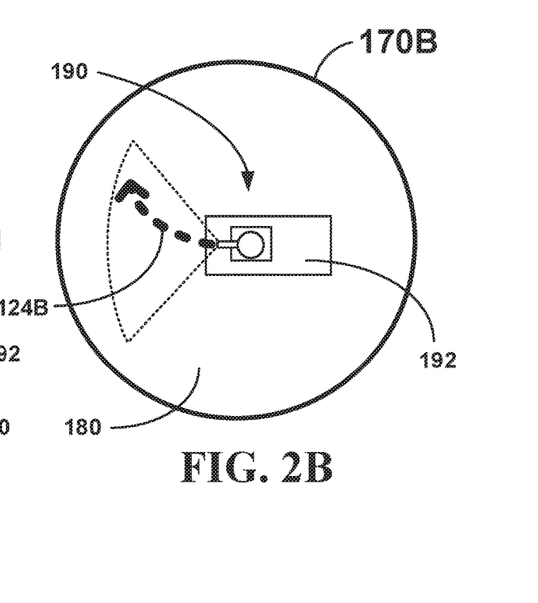
FIG. 2B depicts a top-down view of the guidance element of FIG. 2A providing the first indication.

Pico-projector guidance element 190 may be secured to instrument 192 with a joint such as a ball joint or the like that provides a wide range of movement. For example, pico-projector guidance element 190 may be secured to instrument 192 with substantially 360° of rotation. Controller 110 may control a direction in which pico-projector guidance element 190 is pointed to correspond with a subsequent physical manipulation as determined by controller 110. As depicted in FIGS. 2A and 2B, initially controller 110 is causing pico-projector guidance element 190 to generate directional arrow 124B pointing along a first angular direction. As depicted, pico-projector guidance element 190 is generating directional arrow 124B not only on instrument 192 but also on a surface of the object which instrument 192 is scanning (e.g., on the stomach of a patient upon which instrument 192 is conducting a neonatal ultrasound). In other examples, pico-projector guidance element 190 may be configured/caused to generate guidance feedback only on instrument 192, or on different surfaces (e.g., a wall of the room, or on a ceiling, or on a nearby flat surface, or the like)

Figure 2C:
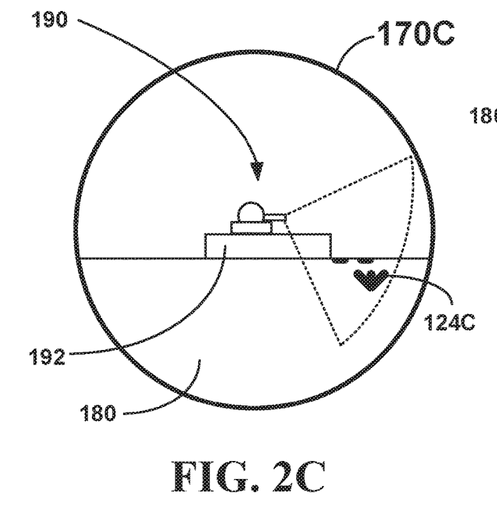
FIG. 2C depicts a side view of the example guidance element of FIG. 2A as actuated to provide a second indication in a second direction.
Figure 2D:
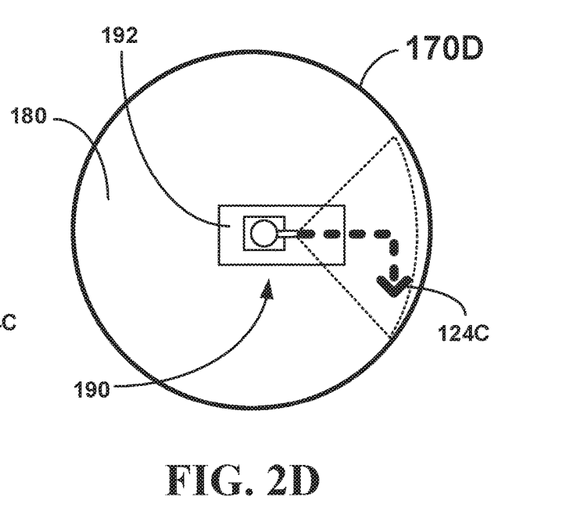
FIG. 2D depicts a top-down view of the guidance element of FIG. 2C providing the second indication.

As discussed above, controller 110 may determine that instrument 192 should be moved according to a subsequent physical manipulation to a new trajectory. In response to this determination, controller 110 generates directional arrow 124C as depicted in FIGS. 2C and 2D. As depicted, pico-projector guidance element 190 may rotate nearly 180 degrees from its previous position to generate directional arrow 124C. In some examples, pico-projector guidance element 190 may further rotate up or down to generate feedback, depending on an orientation of instrument.

Figure 3:
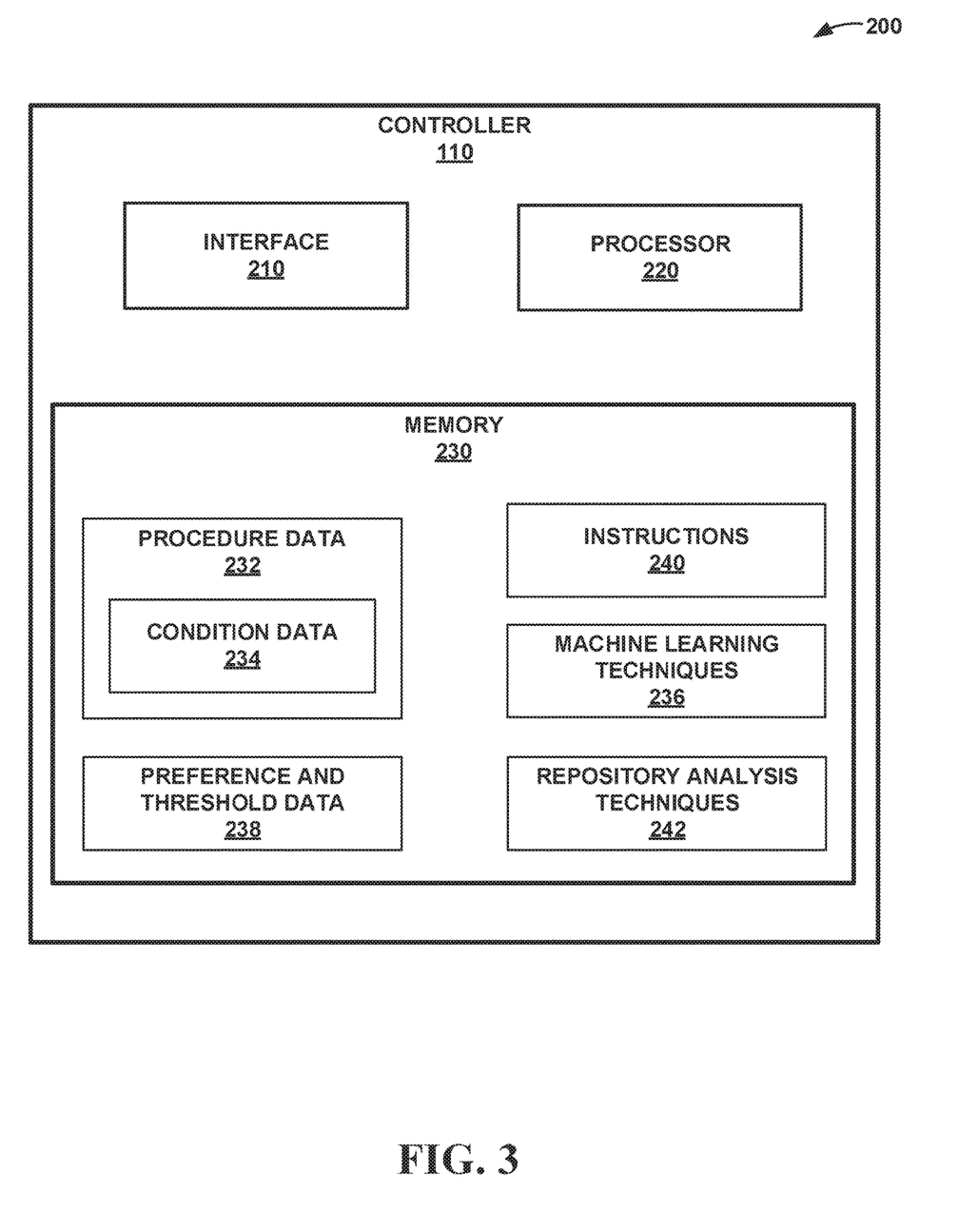
FIG. 3 depicts a conceptual box diagram of a computing system that may be configured to manage physical manipulation feedback of an instrument.

As described above, controller 110 may include computing device 200 with a processor configured to execute instructions stored on a memory to execute the techniques described herein. For example, FIG. 3 is a conceptual box diagram of such computing device 200 of controller 110. While controller 110 is depicted as a single entity (e.g., within a single housing) for the purposes of illustration, in other examples, controller 110 may include two or more discrete physical systems (e.g., within two or more discrete housings). Controller 110 may include interface 210, processor 220, and memory 230. Controller 110 may include any number or amount of interface(s) 210, processor(s) 220, and/or memory(s) 230.

Controller 110 may include components that enable controller 110 to communicate with (e.g., send data to and receive and utilize data transmitted by) devices that are external to controller 110. For example, controller 110 may include interface 210 that is configured to enable controller 110 and components within controller 110 (e.g., such as processor 220) to communicate with entities external to controller 110. Specifically, interface 210 may be configured to enable components of controller 110 to communicate with instrument 120, user device 130, database 140, repositories 150, or the like. Interface 210 may include one or more network interface cards, such as Ethernet cards, and/or any other types of interface devices that can send and receive information. Any suitable number of interfaces may be used to perform the described functions according to particular needs.

As discussed herein, controller 110 may be configured to provide physical manipulation feedback for an instrument. Controller 110 may utilize processor 220 to manage instrument manipulation. Processor 220 may include, for example, microprocessors, digital signal processors (DSPs), application specific integrated circuits (ASICs), field-programmable gate arrays (FPGAs), and/or equivalent discrete or integrated logic circuits. Two or more of processor 220 may be configured to work together to provide physical manipulation feedback for an instrument.

Processor 220 may provide physical manipulation feedback according to instructions 240 stored on memory 230 of controller 110. Memory 230 may include a computer-readable storage medium or computer-readable storage device. In some examples, memory 230 may include one or more of a short-term memory or a long-term memory. Memory 230 may include, for example, random access memories (RAM), dynamic random-access memories (DRAM), static random-access memories (SRAM), magnetic hard discs, optical discs, floppy discs, flash memories, forms of electrically programmable memories (EPROM), electrically erasable and programmable memories (EEPROM), or the like. In some examples, processor 220 may manage physical manipulation feedback according to instructions 240 of one or more applications (e.g., software applications) stored in memory 230 of controller 110.

In addition to instructions 240, in some examples gathered or predetermined data or techniques or the like as used by processor 220 to manage the provision of physical manipulation feedback for an instrument may be stored within memory 230. For example, memory 230 may include information described above that may be stored in database 140, and/or may include substantially all of database 140. For example, as depicted in FIG. 3, memory 230 may include procedure data 232, which includes condition data 234. Procedure data 232 may include one or more steps along which controller 110 may cause an instrument to be physically manipulated during a procedure. The procedure data 232 may include the condition data 234 of conditions that controller 110 checks for during one or more steps of the procedure. The steps may further include biometric conditions or the like that controller may analyze to determine whether or not any of the conditions exist (e.g., using sensors 126 or the like). Procedure data 232 and/or condition data 234 may include one or more templates to which gathered spatial data may be compared to determine a current status or a subsequent step or the like.

Memory 230 may further include machine learning techniques 236 that controller 110 may use to improve a process of managing physical manipulation of an instrument. Machine learning techniques 236 can comprise algorithms or models that are generated by performing supervised, unsupervised, or semi-supervised training on a dataset, and subsequently applying the generated algorithm or model to generate physical manipulation feedback according to preference and threshold data 238.

Machine learning algorithms can include, but are not limited to, decision tree learning, association rule learning, artificial neural networks, deep learning, inductive logic programming, support vector machines, clustering, Bayesian networks, reinforcement learning, representation learning, similarity/metric training, sparse dictionary learning, genetic algorithms, rule-based learning, and/or other machine learning techniques.

For example, the machine learning algorithms can utilize one or more of the following example techniques: K-nearest neighbor (KNN), learning vector quantization (LVQ), self-organizing map (SOM), logistic regression, ordinary least squares regression (OLSR), linear regression, stepwise regression, multivariate adaptive regression spline (MARS), ridge regression, least absolute shrinkage and selection operator (LASSO), elastic net, least-angle regression (LARS), probabilistic classifier, naïve Bayes classifier, binary classifier, linear classifier, hierarchical classifier, canonical correlation analysis (CCA), factor analysis, independent component analysis (ICA), linear discriminant analysis (LDA), multidimensional scaling (MDS), non-negative metric factorization (NMF), partial least squares regression (PLSR), principal component analysis (PCA), principal component regression (PCR), Sammon mapping, t-distributed stochastic neighbor embedding (t-SNE), bootstrap aggregating, ensemble averaging, gradient boosted decision tree (GBRT), gradient boosting machine (GBM), inductive bias algorithms, Q-learning, state-action-reward-state-action (SARSA), temporal difference (TD) learning, apriori algorithms, equivalence class transformation (ECLAT) algorithms, Gaussian process regression, gene expression programming, group method of data handling (GMDH), inductive logic programming, instance-based learning, logistic model trees, information fuzzy networks (IFN), hidden Markov models, Gaussian naïve Bayes, multinomial naïve Bayes, averaged one-dependence estimators (AODE), Bayesian network (BN), classification and regression tree (CART), chi-squared automatic interaction detection (CHAID), expectation-maximization algorithm, feedforward neural networks, logic learning machine, self-organizing map, single-linkage clustering, fuzzy clustering, hierarchical clustering, Boltzmann machines, convolutional neural networks, recurrent neural networks, hierarchical temporal memory (HTM), and/or other machine learning techniques.

Memory 230 may also include preference and threshold data 238. Preferences and threshold data 238 may include thresholds as described herein that indicate whether or not gathered spatial data is sufficient. Further, preferences may include an amount or extent of guidance that a user may want to have during a procedure. For example, a new medical professional may request that controller 110 provide feedback regarding physical manipulation of a medical instrument. However, this medical professional may know about the medical conditions of a procedure, such that the medical professional may not require and/or desire feedback reminding a user to check for a subsequent condition. However, the medical professional may desire that controller 110 provide feedback regarding validation that gathered spatial data passes thresholds for accuracy as described herein. In this way, controller 110 may reference preference and threshold data 238 to tailor a manner in which controller 110 provides feedback regarding instrument manipulation for different users.

Memory 230 may include repository analysis techniques 242 that controller 110 may use to identify whether data stored in repositories 150 matches spatial data or impacts procedure data 232 and/or condition data 234. For example, repository analysis techniques 242 may include image recognition techniques such as pattern matching, shape identification, image recognition techniques, and/or object tracking techniques. Using such techniques, controller 110 may match one or more images from spatial data gathered via instrument 120 to images from one or more repositories 150. Additionally, or alternatively, controller 110 may use these techniques to match one or more images from procedure data 232 and/or condition data 234 to images from repositories 150.

Further, repository analysis techniques 242 may include NLP techniques that may be used to learn more about a matched image of repositories once identified as described above. For example, NLP techniques may include semantic similarity, syntactic analysis, and ontological matching to identify details from images matched using image recognition techniques. For example, in some embodiments, processor 220 may be configured to parse comments from a medical journal or the like in repositories 150 to determine semantic features (e.g., word meanings, repeated words, keywords, etc.) and/or syntactic features (e.g., word structure, location of semantic features in headings, title, etc.) that discuss or define a related image or plot of spatial data from repositories 150. Ontological matching could be used to map semantic and/or syntactic features to a particular procedure and/or condition. The concept can then be used to determine how to physically manipulate the instrument to gather spatial information on this condition. In this way, using NLP techniques and image recognition techniques, controller 110 may, e.g., identify procedure and/or condition data from repositories 150 that relate to spatial data as gathered by instrument 120 that does not match a template of procedure data 232 and/or condition data 234.

Figure 4:
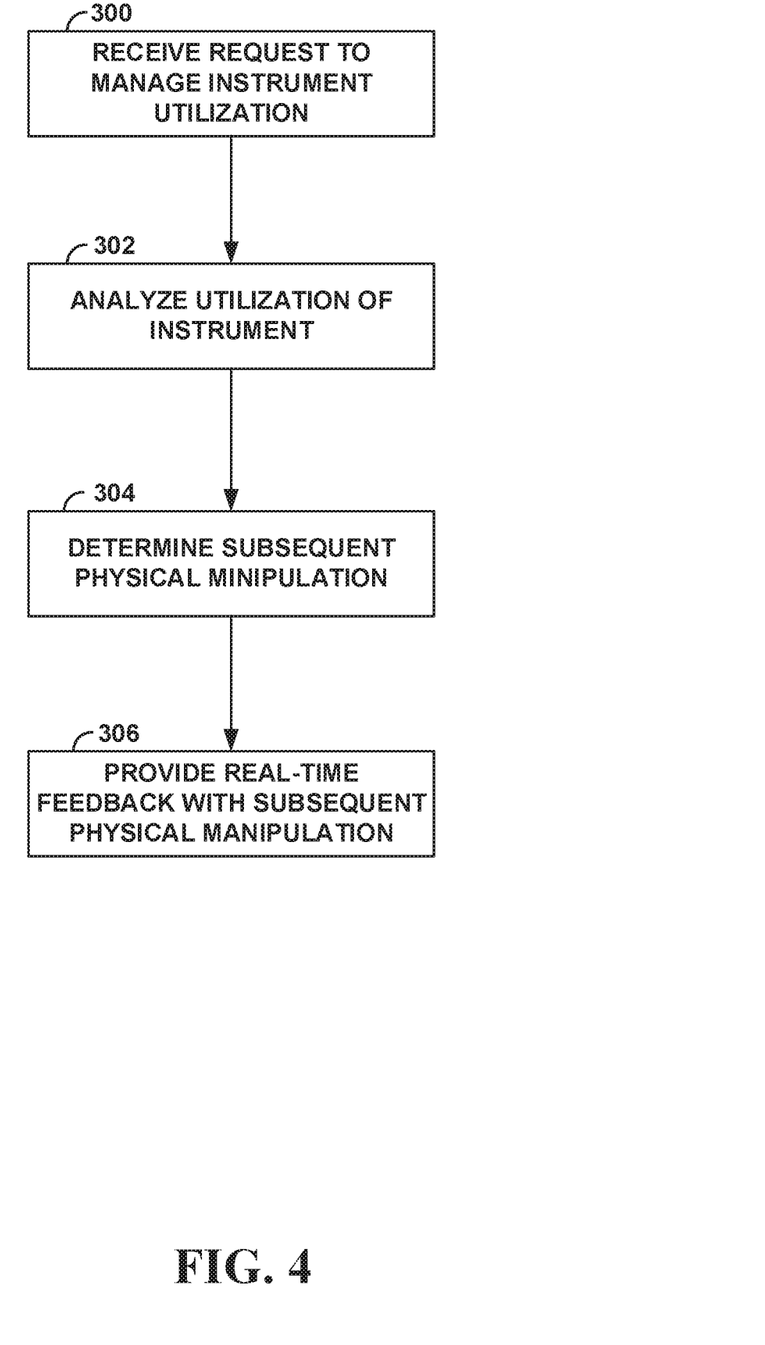
FIG. 4 depicts an example flowchart of managing physical manipulation feedback of an instrument.

Using these components, controller 110 may provide feedback regarding physical manipulation or the like as discussed herein. For example, controller 110 may provide physical manipulation feedback according to the flowchart depicted in FIG. 4. The flowchart of FIG. 4 is discussed with relation to FIG. 1 for purposes of illustration, though it is to be understood that other systems may be used to execute the flowchart of FIG. 4 in other examples. Further, in some examples controller 110 may provide feedback regarding physical manipulation differently than the flowchart of FIG. 4, or controller 110 may provide feedback regarding physical manipulation via a similar method with more or less steps in a different order, or the like. Further, although the method of FIG. 4 is described in terms of a medical procedure, in other examples controller 110 may provide physical manipulation feedback for other types of procedures (such as an inspection procedure using a laser scanning instrument 120 or the like), such that aspects of this disclosure are not limited to medical procedures.

Controller 110 may receive a request to provide feedback regarding physical manipulation of instrument 120 (300). For example, a user may send a request to controller 110 from user device 130 over network 160. The request may include a specific procedure for which for which the user requests that controller 110 provide physical manipulation feedback. For example, instrument 120 may be a medical instrument such as an ultrasound probe, and the request may indicate that the procedure is a neonatal ultrasound.

Controller 110 may analyze the utilization of instrument 120 (302). Analyzing the utilization may include identifying a current orientation of instrument 120. A current orientation may include a relative location at which instrument 120 is gathering spatial data relative to target object 134, a speed at which instrument 120 is moving, a trajectory of instrument 120, an extent to which instrument 120 is pressed against a patient (e.g., as measured by pressure sensor 126), or the like. Controller 110 may both analyze spatial data as well as utilize data from one or more sensors 126 of instrument to determine current utilization.

Controller 110 may identify a subsequent physical manipulation (304). For example, controller 110 may identify a subsequent physical manipulation that may gather spatial data for a next step of the medical procedure. For another example, controller 110 may identify that previously gathered spatial data did not satisfy one or more thresholds, such that a subsequent physical manipulation includes regathering replacement spatial data for that region and/or condition.

Controller 110 may provide real-time feedback with a subsequent physical manipulation that will cause instrument 120 to gather such additional spatial data (306). Controller 110 may provide this feedback using guidance elements 122 to generate text or direction arrows 124 or haptic feedback or audible commands or the like. Additionally, or alternatively, controller 110 may provide this feedback on display 132 of user device 130 that is depicting some or all of spatial data as gathered by instrument 120.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method comprising:
receiving spatial data regarding an ongoing physical manipulation of an ultrasound probe that is configured to gather the spatial data via physical manipulation of the ultrasound probe for a procedure;
determining a current orientation of the ultrasound probe;
determining additional spatial data to gather for the procedure;
determining a subsequent physical manipulation on how to physically maneuver the ultrasound probe relative to the current orientation to gather the additional spatial data; and
providing one or more queues that include visual instructions as projected onto the ultrasound probe on how to execute the subsequent physical manipulation via one or more pico-projectors located on the ultrasound probe.

2. The computer-implemented method of claim 1, wherein the current orientation of the ultrasound probe is determined using the spatial data.

3. The computer-implemented method of claim 1, wherein the visual instructions include at least one of:
a directional arrow that indicates a subsequent direction of the ultrasound probe for the subsequent physical manipulation;
an angular arrow that indicates a subsequent angular orientation of the ultrasound probe for the subsequent physical manipulation; and
a speed instruction that indicates a subsequent speed of the ultrasound probe for the subsequent physical manipulation.

4. The computer-implemented method of claim 1, further comprising depicting, on a user device, a representation of the spatial data gathered by the ultrasound probe during the procedure.

5. The computer-implemented method of claim 1, wherein the visual instructions include a directional arrow on the representation of the spatial data on a user device indicating the subsequent physical manipulation.

6. A system comprising:
an ultrasound probe configured to gather spatial data via physical manipulation of the ultrasound probe;
a processor; and
a memory in communication with the processor, the memory containing instructions that, when executed by the processor, cause the processor to:
receive data regarding an ongoing physical manipulation of the ultrasound probe for a procedure;
determine a current orientation of the ultrasound probe;
determine additional spatial data to gather for the procedure;
determine a subsequent physical manipulation on how to physically maneuver the ultrasound probe relative to the current orientation to gather the additional spatial data; and
provide one or more queues that include visual instructions as projected onto the ultrasound probe on how to execute the subsequent physical manipulation via one or more pico-projectors located on the ultrasound probe.

7. The system of claim 6, wherein the visual instructions include at least one of:
a directional instruction that indicates a subsequent direction of the ultrasound probe for the subsequent physical manipulation;
an angular instruction that indicates a subsequent angular orientation of the ultrasound probe for the subsequent physical manipulation; or
a speed instruction that indicates a subsequent speed of the ultrasound probe for the subsequent physical manipulation.

8. The system of claim 6, wherein the memory further contains instructions that, when executed by the processor, cause the processor to depict, on a user device, a representation of the spatial data gathered by the ultrasound probe during the procedure.

9. The system of claim 8, wherein the visual instructions include a directional arrow on the representation of the spatial data on a user device indicating the subsequent physical manipulation.

10. A computer program product, the computer program product comprising a computer readable storage medium having program instructions embodied therewith, the program instructions executable by a computer to cause the computer to:
receive data regarding an ongoing physical of an ultrasound probe that is configured to gather spatial data via physical manipulation of the ultrasound probe for a procedure;
determine a current orientation of the ultrasound probe;
determine additional spatial data to gather for the procedure;
determine a subsequent physical manipulation on how to physically maneuver the ultrasound probe relative to the current orientation to gather the additional spatial data; and
provide one or more queues that include visual instructions as projected onto the ultrasound probe on how to execute the subsequent physical manipulation via one or more pico-projectors located on the ultrasound probe.

* * * * *